US012810417B2

(12) United States Patent
Jhong et al.

(10) Patent No.: US 12,810,417 B2
(45) Date of Patent: Nov. 24, 2026

(54) AUTOMATIC SCALP SEBUM CLASSIFICATION SYSTEM AND METHOD FOR AUTOMATIC CLASSIFICATION OF SCALP SEBUM

(71) Applicant: MacroHI Co., Ltd., New Taipei City (TW)

(72) Inventors: Sin-Ye Jhong, New Taipei City (TW); Chih-Hsien Hsia, Taipei City (TW); Chun-Wei Chen, New Taipei City (TW)

(73) Assignee: MacroHI Co., Ltd., New Taipei City (TW)

( * ) Notice: Subject to any disclaimer, the term of this patent is extended or adjusted under 35 U.S.C. 154(b) by 293 days.

(21) Appl. No.: 18/399,702

(22) Filed: Dec. 29, 2023

(65) Prior Publication Data

US 2025/0173858 A1 May 29, 2025

(30) Foreign Application Priority Data

Nov. 23, 2023 (CN) ......................... 202311571500.6

(51) Int. Cl.
*G06T 7/00* (2017.01)
*G06N 3/045* (2023.01)
(Continued)

(52) U.S. Cl.
CPC ........... *G06T 7/0012* (2013.01); *G06N 3/045* (2023.01); *G06N 3/048* (2023.01); *G06N 3/084* (2013.01);
(Continued)

(58) Field of Classification Search
CPC ......... G06T 7/0012; G06T 2207/10004; G06T 2207/20021; G06T 2207/20081;
(Continued)

(56) References Cited

U.S. PATENT DOCUMENTS 6,836,554 B1 * 12/2004 Bolle ........................ G07C 9/37 902/4
7,120,607 B2 * 10/2006 Bolle ................... G06Q 20/401 902/4
(Continued)

FOREIGN PATENT DOCUMENTS

CN 114419020 A 4/2022
CN 116955983 A 10/2023
(Continued)

OTHER PUBLICATIONS

English Translation of KR102551815B1 to Ecomine Inc. acquired via Espacenet (Year: 2023).*
(Continued)

*Primary Examiner* — Aaron W Carter
(74) *Attorney, Agent, or Firm* — Bruce Stone LLP; Joseph A. Bruce

(57) ABSTRACT

The present disclosure relates to an automatic scalp sebum classification system and a method for automatic classification of scalp sebum. A high-resolution image of a part of the scalp is captured and divided into non-overlapping blocks. Random rotation and position swapping of the blocks are performed for data augmentation and privacy preservation. Each block is then converted into a one-dimensional vector, to which positional information is added through learnable embedding vectors. The vectors are input into a visual transformation model that outputs a sebum classification label. The automatic scalp sebum classification system and method for automatic classification of scalp sebum offer advantages in speed, accuracy, and privacy preservation over traditional and other AI-based methods.

9 Claims, 8 Drawing Sheets

(51) Int. Cl.
*G06N 3/048* (2023.01)
*G06N 3/084* (2023.01)
*G16H 30/40* (2018.01)
*G16H 50/20* (2018.01)

(52) U.S. Cl.
CPC ............. *G16H 30/40* (2018.01); *G16H 50/20* (2018.01); *G06T 2207/10004* (2013.01); *G06T 2207/20021* (2013.01); *G06T 2207/20081* (2013.01); *G06T 2207/20084* (2013.01); *G06T 2207/30088* (2013.01)

(58) Field of Classification Search
CPC ........... G06T 2207/20084; G06T 2207/30088; G06N 3/045; G06N 3/048; G06N 3/084; G16H 30/40; G16H 50/20; G06V 10/764; G06V 10/7715; G06V 40/10; G06V 10/82; G06V 10/774; G06V 2201/03; A61B 5/446; G06F 21/6245
See application file for complete search history.

(56) References Cited

U.S. PATENT DOCUMENTS

| | | | | |
|---|---|---|---|---|
| 10,650,286 | B2 * | 5/2020 | Ben-Ari | G06F 18/2411 |
| 12,086,983 | B2 * | 9/2024 | Jhong | G06T 7/0012 |
| 2002/0030359 | A1 * | 3/2002 | Bergenek | G06Q 20/40145 283/67 |
| 2004/0145656 | A1 * | 7/2004 | Betra | A61B 5/7445 705/16 |
| 2011/0229045 | A1 * | 9/2011 | Yu | G06V 20/10 382/224 |
| 2022/0335614 | A1 * | 10/2022 | Punyani | G06Q 10/0833 |
| 2022/0375601 | A1 * | 11/2022 | Punyani | G16H 20/00 |
| 2023/0178238 | A1 * | 6/2023 | Park | G16H 50/20 705/2 |
| 2024/0404094 | A1 * | 12/2024 | Jhong | A61B 5/7264 |
| 2025/0173858 | A1 * | 5/2025 | Jhong | G06V 10/764 |
| 2025/0204839 | A1 * | 6/2025 | Zhou | G06N 3/048 |

FOREIGN PATENT DOCUMENTS

| | | | |
|---|---|---|---|
| KR | 102551815 | B1 | 7/2023 |
| TW | 202312096 | A | 3/2023 |

OTHER PUBLICATIONS

Ktim erar., "Development of a new classification and scoring system for scalp conditions: Scalp Photographic Index (SPI)", Mar. 27, 2023, Journal of Dermatological Treatment.
Krishna et al., "LesionAid Vision Transformers-based Skin Lesion Generation and Classification", Feb. 2, 2022.
Chang et al., "ScalpEye: A Deep Learning-Based Scalp Hair Inspection and Diagnosis System for Scalp Health", Jul. 21, 2020, IEEE Access.
Al-Hammuri et al., "Vision transformer architecture and applications in digital health a tutorial and survey", Jul. 10, 2023, Springer Open.
Mukhopadhyay Sudipta et al, Toward more Robust Skull striping using Custom transformer and Combined Hausdorff loss, Computing and Communication Technologies (CONECCT), Jul. 14, 2023, pp. 1-6, IEEE.

* cited by examiner

10

AUTOMATIC SCALP SEBUM CLASSIFICATION SYSTEM AND METHOD FOR AUTOMATIC CLASSIFICATION OF SCALP SEBUM

FIELD OF THE DISCLOSURE

The present disclosure relates to the field of computer vision and machine learning, specifically, an automatic scalp sebum classification system and a method for automatic classification of scalp sebum using a visual transformation model.

BACKGROUND OF THE INVENTION

This disclosure primarily pertains to the field of computer vision and machine learning. More specifically, it involves a system and method for automatically classifying scalp sebum properties using a visual transformation model.

Traditional methods for determining scalp sebum properties, such as dry, neutral, or oily, usually rely on manual inspection and evaluation. These methods are not just time-consuming, but also prone to human error and variability due to subjective judgement. Furthermore, the mental state or professional knowledge of the evaluator may affect the manual method, leading to inconsistent results.

Some existing computer vision techniques have been used to automate this process. However, these methods often struggle to handle subtle feature differences that are pivotal for accurate sebum classification. Additionally, the data used for training and validation in these methods often suffer from class imbalance, requiring data augmentation techniques to improve model performance.

Moreover, privacy issues have been raised for the use of high-resolution scalp images, especially when these images are stored or transmitted for analysis.

Therefore, there is a demand for a more reliable, efficient, and privacy-protecting method for automatic classification of scalp sebum. This method ought to handle subtle feature differences and class imbalance in the data, while ensuring the privacy of the scalp images being analyzed.

SUMMARY OF THE INVENTION

This disclosure introduces a system and method for automatic classification of scalp sebum using a visual transformation model. The goal of this innovation is to overcome the limitations of existing methods and provide a solution that is both effective and reliable. Traditional methods typically rely on manual inspection, which is not just time-consuming, but also prone to human error and subjectivity. This innovation automates this process, thereby eliminating these issues.

The system captures a high-resolution image of a part of the scalp, then divides these images into non-overlapping blocks. Each block is transformed into a one-dimensional vector. Learnable positional embeddings are added to these vectors to retain spatial information lost in the flattening process. These enhanced vectors are then input into a visual transformation model, which processes the data and outputs a classification label indicating scalp sebum properties, such as dry, neutral, or oily.

A distinctive feature of this innovation is the optional data augmentation module, which performs random rotation and position swapping of the blocks. This not just enhances the performance of the model, addressing the issue of class imbalance, but also adds a layer of privacy protection.

By automating the classification of scalp sebum properties and combining advanced machine learning techniques, this innovation provides a comprehensive and effective solution to the challenges faced by existing methods. It effectively handles subtle feature differences, resolves class imbalance in training data, and ensures the privacy of the scalp images being analyzed.

BRIEF DESCRIPTION OF THE DRAWINGS

The objects, spirits, and advantages of the preferred embodiments of the present disclosure will be readily understood by the accompanying drawings and detailed descriptions, wherein.

DESCRIPTION OF THE PREFERRED EMBODIMENTS

Figure 1:
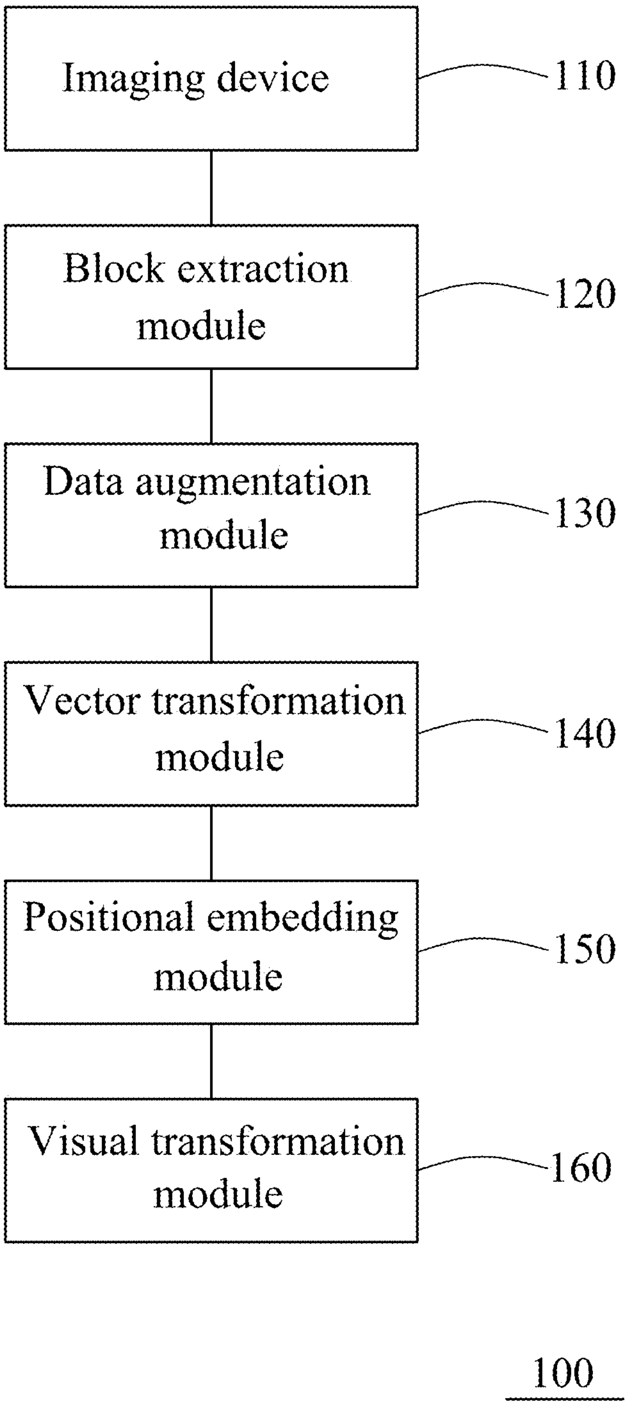
FIG. 1 illustrates a block diagram of one implementation of the automatic scalp sebum classification system of this disclosure.
Figure 2:
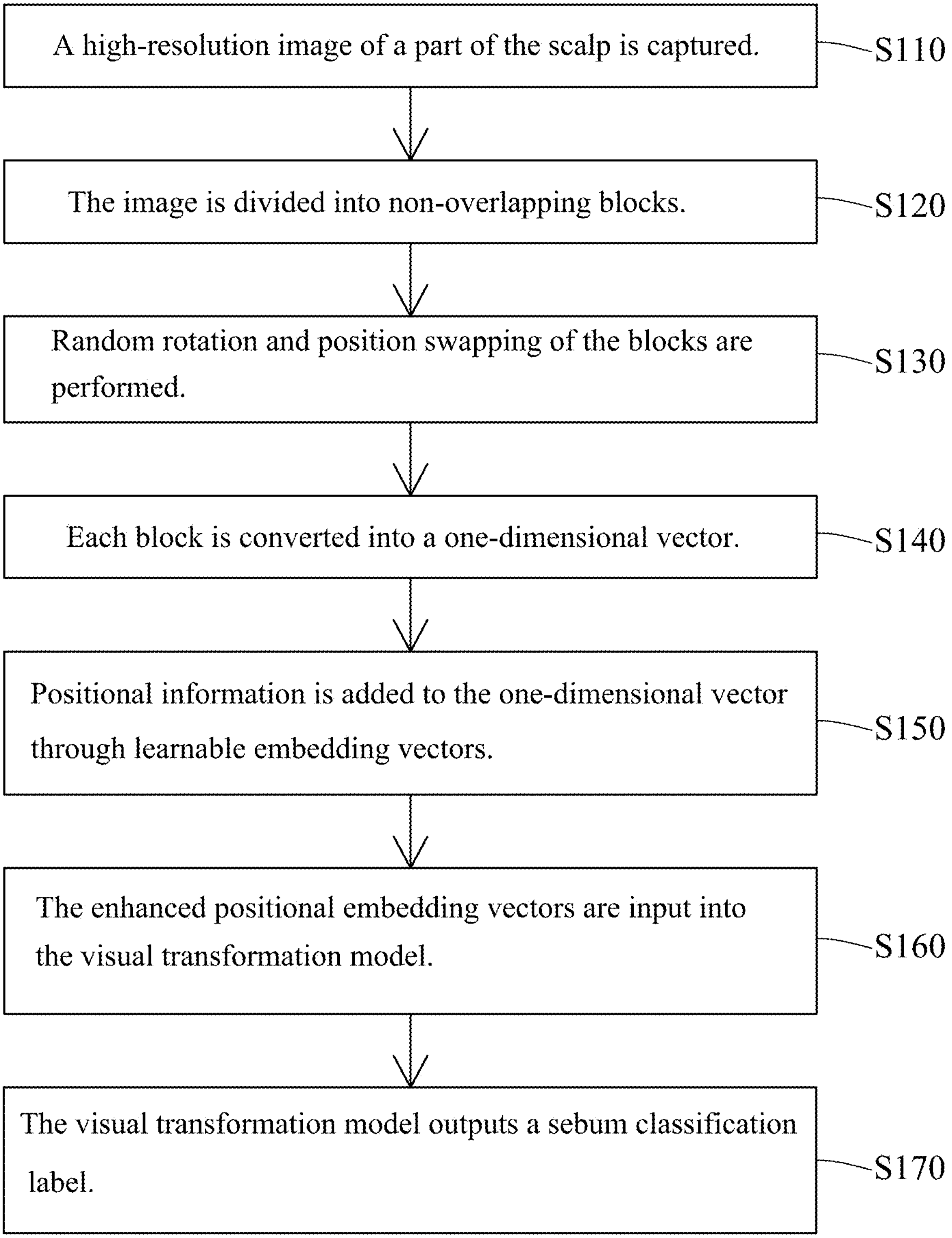
FIG. 2 illustrates a flowchart of one implementation of the automatic scalp sebum classification method of this disclosure.

Referring to FIGS. 1 and 2, FIG. 1 illustrates a block diagram of one implementation of the automatic scalp sebum classification system of this disclosure, and FIG. 2 illustrates a flowchart of one implementation of the automatic scalp sebum classification method of this disclosure. Referring to step S110, the automatic scalp sebum classification system 100 of this implementation first captures a high-resolution image of a part of the scalp. This process can be performed using various imaging devices 110 capable of capturing detailed images of the scalp surface. The captured scalp image serves as the main input to the automatic scalp sebum classification system 100, providing the original data for determining sebum properties.

Once the image is captured, step S120 is executed, and the input image is divided into non-overlapping blocks. This division process is carried out by the block extraction module 120, which divides the high-resolution scalp image into smaller, more manageable parts. Each block represents a specific area of the scalp, and this block-based approach allows for more detailed and localized analysis of scalp sebum properties later.

After block extraction, step S130 is executed, and the data augmentation module 130 performs random rotation and position swapping of the blocks. This step introduces variability into the data, which helps to enhance the robustness of the artificial intelligence model by exposing it to a wider range of data scenarios. In addition, the random rotation and position swapping of the blocks also serve as a privacy protection measure. By scrambling the original arrangement of the blocks, the automatic scalp sebum classification system 100 makes it difficult to reconstruct the original scalp image, thereby protecting individual privacy.

Then, step S140 is executed, and each block is converted into a one-dimensional vector by the vector transformation module 140. This transformation process involves flattening the two-dimensional block into a one-dimensional pixel value array. The resulting vector retains the pixel intensity information of the block, but its format is more suitable for processing by subsequent components of the system.

Next, step S150 is executed, and positional information is added to the one-dimensional vector through learnable embedding vectors. This step is carried out by the positional embedding module 150, which adds a layer of spatial information to the vector. The learnable embedding vectors encode the relative position of the block 11 in the original scalp image, allowing the automatic scalp sebum classification system 100 to retain some spatial context.

Figure 5A:
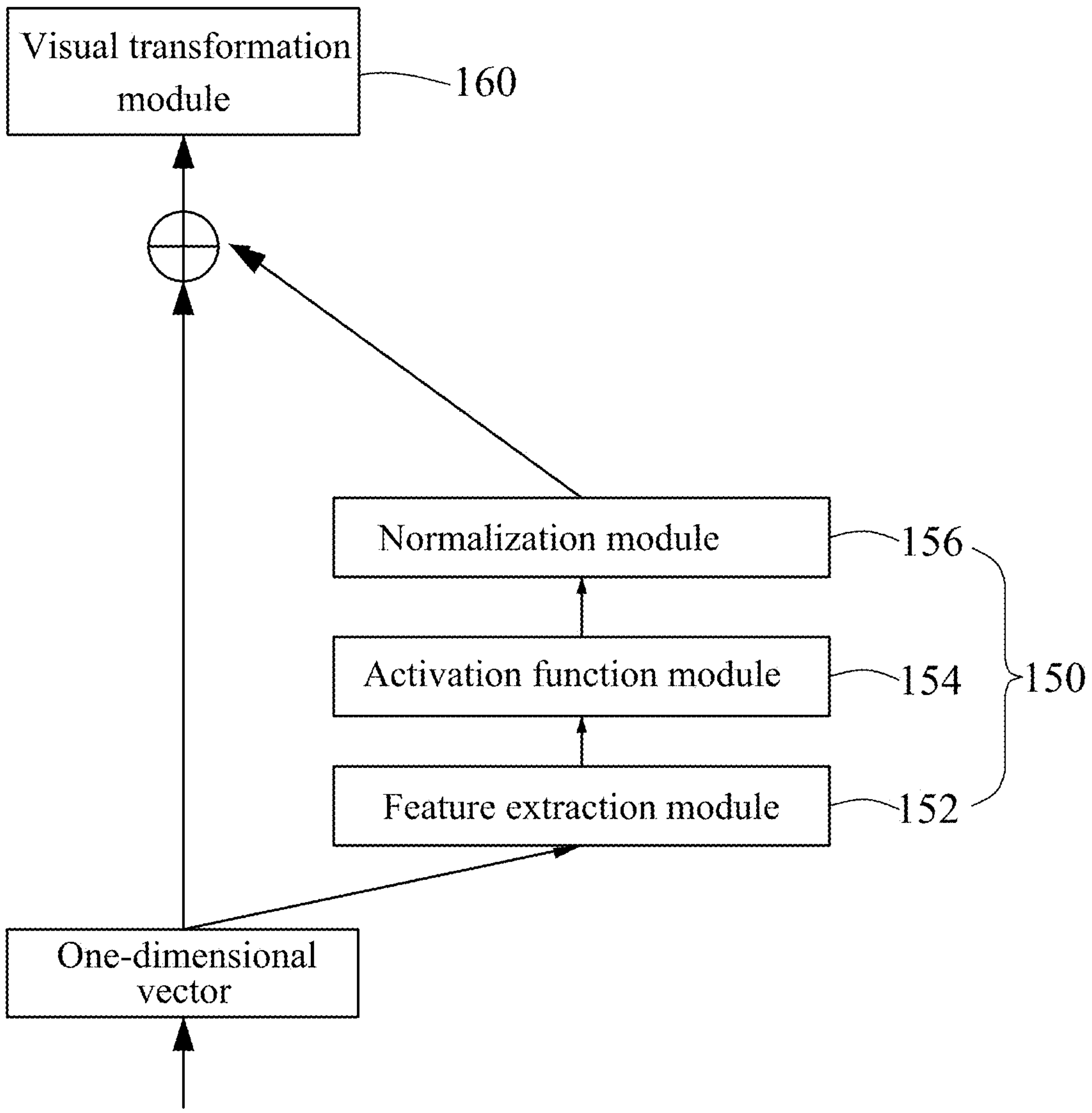
FIG. 5A illustrates a structural diagram of the positional embedding module in this disclosure.

It is worth noting that the positional embedding module 150 can have various possible configurations. Referring to FIG. 5A, the positional embedding module 150 can include at least one feature extraction module 152, at least one activation function module 154, and at least one normalization module 156. Among them, the feature extraction module 152 is used to transform the one-dimensional vector of the block, the activation function module 154 is used to introduce non-linearity, and the normalization module 156 is used to normalize the output value.

Next, step S160 is executed, and the enhanced positional embedding vectors are input into the visual transformation model 160. The visual transformation model 160 is an artificial intelligence model designed for image analysis tasks. It contains a plurality of layers of self-attention mechanisms and feedforward neural networks, which work together to analyze the input vectors and extract meaningful features related to scalp sebum properties.

Finally, step S170 is executed, and the visual transformation model 160 outputs a sebum classification label. This label indicates the sebum properties of the scalp part represented by the input image, and can be one of the following three categories: dry, neutral, or oily. The classification label serves as the final output of the automatic scalp sebum classification system 100, providing a concise indication of the analyzed scalp sebum properties.

Figure 3A:
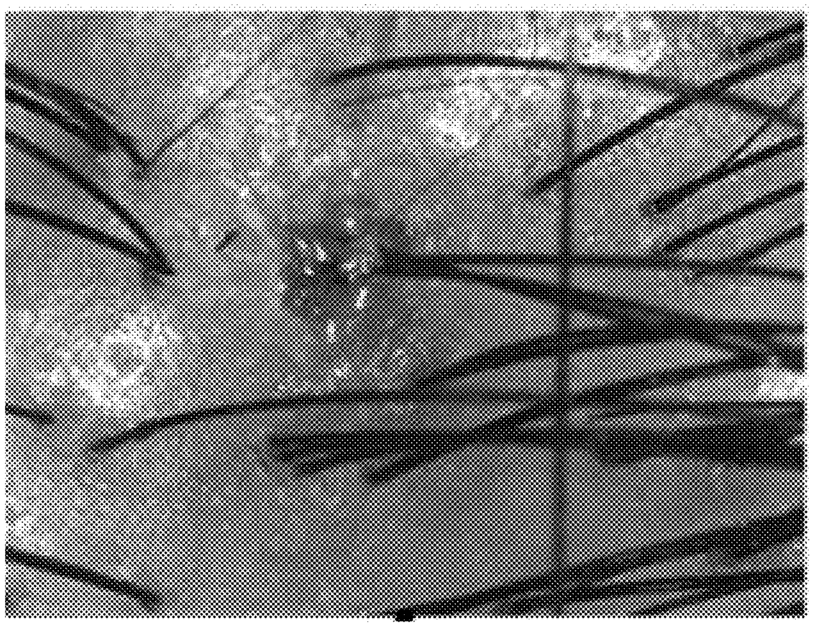
FIGS. 3A to 3C illustrate schematic diagrams of the process of converting images into blocks in this disclosure.

Next, we will provide a more detailed description of the aforementioned automatic scalp sebum property classification system and method. Please continue to refer to FIGS. 1 and 2. At the initial stage of the automatic classification process, that is, step S110, a high-resolution image of a part of the scalp (as shown in FIG. 3A) is captured. This image capture can be performed using various imaging devices 110, such as digital cameras, smartphone cameras, or specialized dermatological imaging devices. The position of the imaging device 110 is set to be able to capture a clear and detailed view of a part of the scalp. The resolution of the captured image 10 is high enough to allow for detailed analysis of the scalp surface, including texture, color, and other visual characteristics that may indicate sebum properties.

Figure 3B:
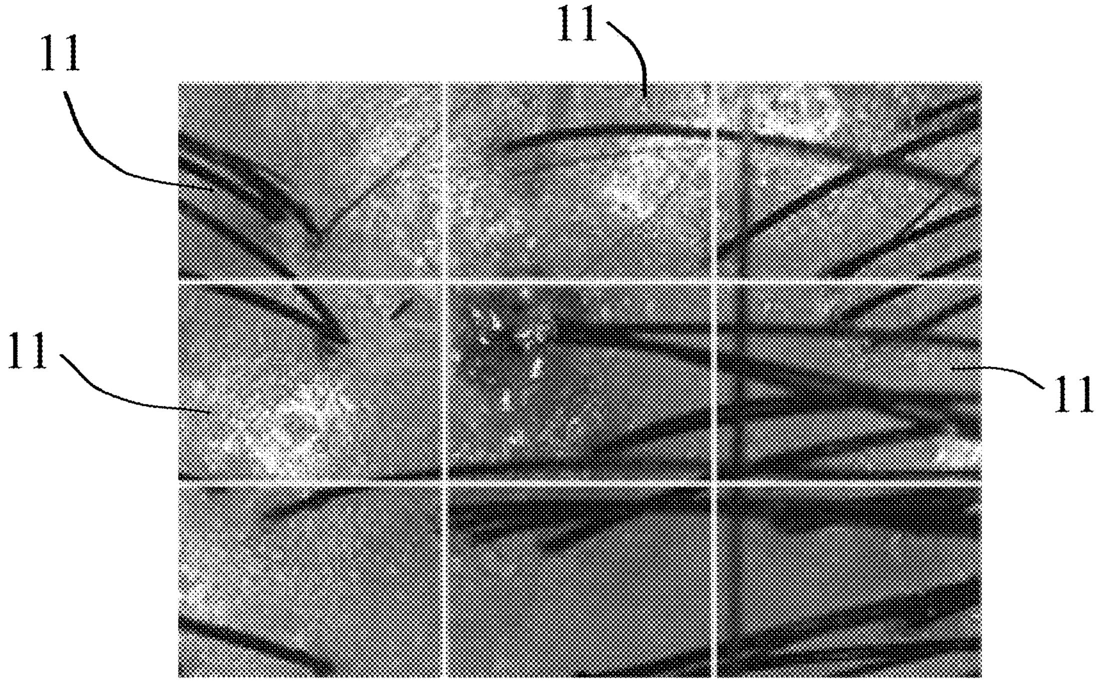

Once a high-resolution image of a part of the scalp has been captured, it is processed by the block extraction module 120. As shown in step S120, the block extraction module 120 is responsible for dividing the image into non-overlapping blocks 11 (as shown in FIG. 3B). The division process involves splitting the image into smaller parts, namely: blocks 11, each part representing a specific area of the scalp, and the blocks 11 are square-shaped. The size of the blocks 11 can be determined based on various factors, such as the resolution of the image, the level of detail desired in the analysis, and the available computational resources. Each block 11 is considered an independent unit of analysis, allowing for more localized and detailed inspection of scalp sebum properties.

The design of the block extraction process is to ensure that each block 11 contains enough information for subsequent analysis. To this end, the blocks 11 are extracted in such a way that they cover the full range of the scalp part depicted in the image, without overlapping with other blocks. This non-overlapping arrangement ensures that each area of the scalp is analyzed once, preventing redundancy in the analysis. In addition, the non-overlapping arrangement also helps to maintain the spatial integrity of the original image, as each block 11 corresponds to a specific and distinct area of the scalp.

In summary, the process of capturing a high-resolution image of a part of the scalp and dividing these images into non-overlapping blocks 11 ensures that the automatic scalp sebum property classification system 100 can obtain detailed and localized visual information about the scalp, which is then used to determine sebum properties in a reliable and efficient manner.

Figure 3C:
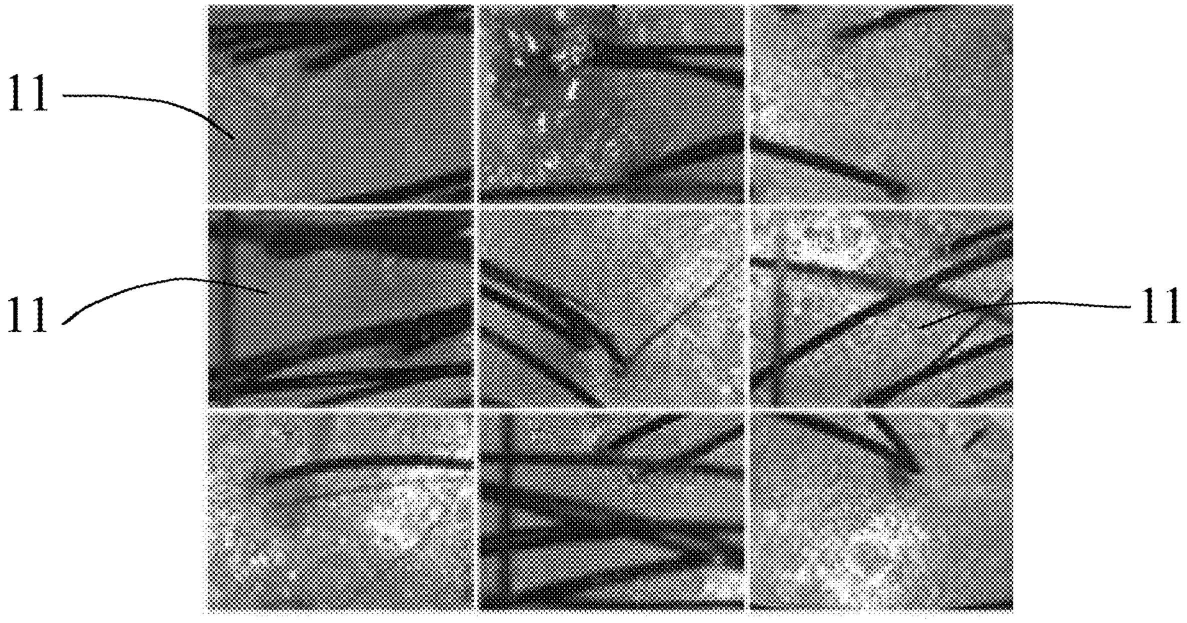

After extracting blocks 11 from the high-resolution scalp image 10, the automatic scalp sebum property classification system 100 uses the data augmentation module 130 to perform random rotation and position swapping of the blocks 11 (as shown in FIG. 3C). This data augmentation module 130 introduces a degree of randomness, which has two main purposes.

First, the random rotation and position swapping of the blocks 11 help to enhance the robustness of the visual transformation model 160. In machine learning, robustness refers to the ability of a model to maintain its performance in the face of changes in input data. By introducing randomness, the automatic scalp sebum property classification system 100 exposes the visual transformation model 160 to a wider range of data scenarios, thereby encouraging the visual transformation model 160 to learn more general and robust representations of scalp sebum properties. This is particularly beneficial in addressing the problem of class imbalance, where some sebum property categories may be underrepresented in the training data. By randomly rotating and swapping the positions of the blocks, the automatic scalp sebum property classification system 100 effectively increases the diversity of training data for each category, helping to mitigate the impact of class imbalance and improve the overall performance of the model.

Second, the random rotation and position swapping of the blocks 11 serve as a privacy protection measure. In this implementation, privacy protection refers to the protection of the personal identity of the scalp image being analyzed. By scrambling the original arrangement of the blocks 11, it becomes difficult to reconstruct the original scalp image from the processed data. This means that even if someone obtains the data without authorization, they cannot identify the individual from the scrambled blocks. This feature is particularly valuable in applications where personal privacy is paramount, such as in medical diagnosis or personal care applications.

In summary, the data augmentation module 130 enhances the robustness of the visual transformation model 160 and protects personal privacy by performing random rotation and position swapping of the blocks 11. By performing random rotation and position swapping of the blocks 11, the system can handle subtle feature differences and class imbalance in the data, while ensuring the privacy of the scalp images being analyzed.

After the data augmentation process, step S140 is executed, and the automatic scalp sebum classification system 100 continues to convert each block 11 into a one-dimensional vector. This conversion is performed by the vector transformation module 140, which transforms the two-dimensional block 11 into a one-dimensional pixel value array. The transformation process involves flattening the block 11, which basically involves rearranging the pixel values from a two-dimensional grid into a one-dimensional sequence. This process retains the pixel intensity information of the block 11, but presents it in a format more suitable for processing by subsequent components of the automatic scalp sebum classification system 100.

Once the block 11 has been converted into a one-dimensional vector, step S150 is executed, and the automatic scalp sebum classification system 100 adds positional information to these one-dimensional vectors through learnable embedding vectors. This step is performed by the positional embedding module 150, which is designed to encode the relative position of the block 11 in the original scalp image. The learnable embedding vectors are basically a set of parameters learned during the training process of the visual transformation model. These parameters represent the spatial relationship between the blocks 11, thus allowing the system to retain some spatial context, despite the flattening process.

Figure 4:
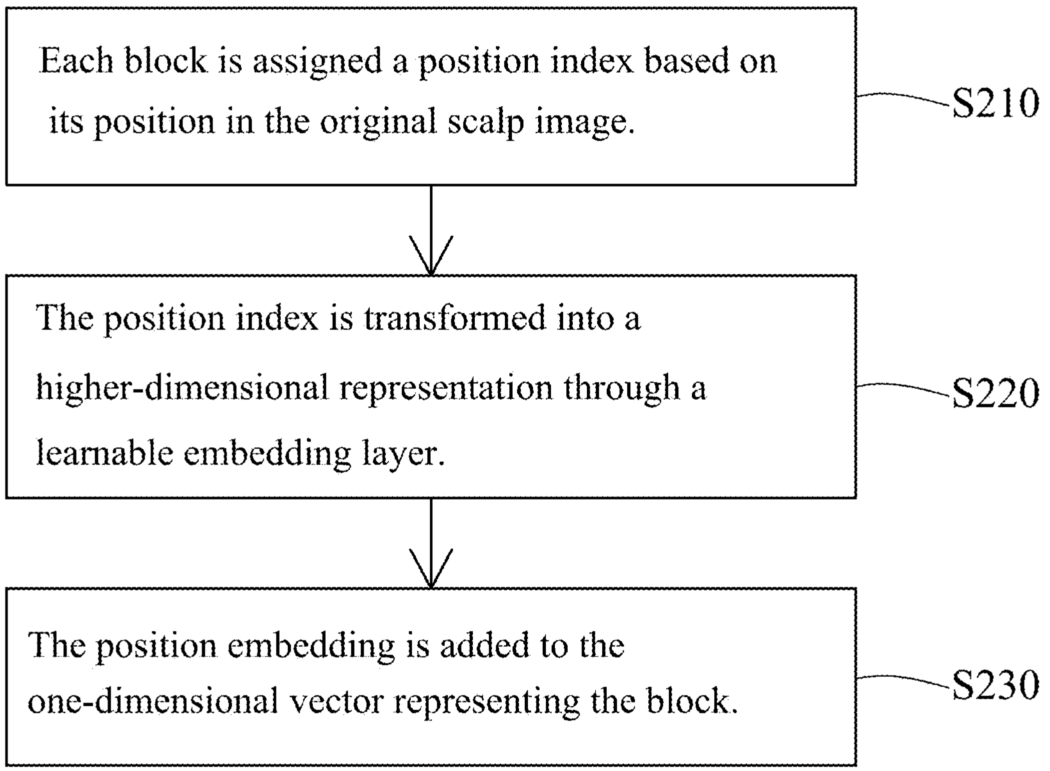
FIG. 4 illustrates a flowchart of the process of adding positional information to a one-dimensional vector in this disclosure.

The process of adding positional information to a one-dimensional vector involves a series of operations, please also refer to FIG. 4. First, as shown in step S210, each block 11 is assigned a position index based on its position in the original scalp image 10. This position index serves as a kind of spatial metadata, providing additional context about the position of the block. Then, as shown in step S220, the position index is transformed into a higher-dimensional representation through a learnable embedding layer. This layer is basically a lookup table with learnable parameters, mapping the position index to a dense vector of real numbers. The resulting vector, called a position embedding, encodes the relative position of the block in the scalp image.

Then, as shown in step S230, the position embedding is added to the one-dimensional vector representing the block 11. This addition operation effectively combines the pixel intensity information of the block with the spatial information encoded in the position embedding. The resulting vector now contains pixel intensity and position information, and is then prepared to be input into the visual transformation model 160 for further processing.

In summary, the process of converting each block 11 into a one-dimensional vector and adding positional information through learnable embeddings is a pivotal step in the workflow of the automatic scalp sebum classification system 100. This process ensures that the visual transformation model 160 receives comprehensive input data containing pixel intensity and spatial information, thereby achieving a more accurate and global perception of scalp sebum properties.

Figure 5B:
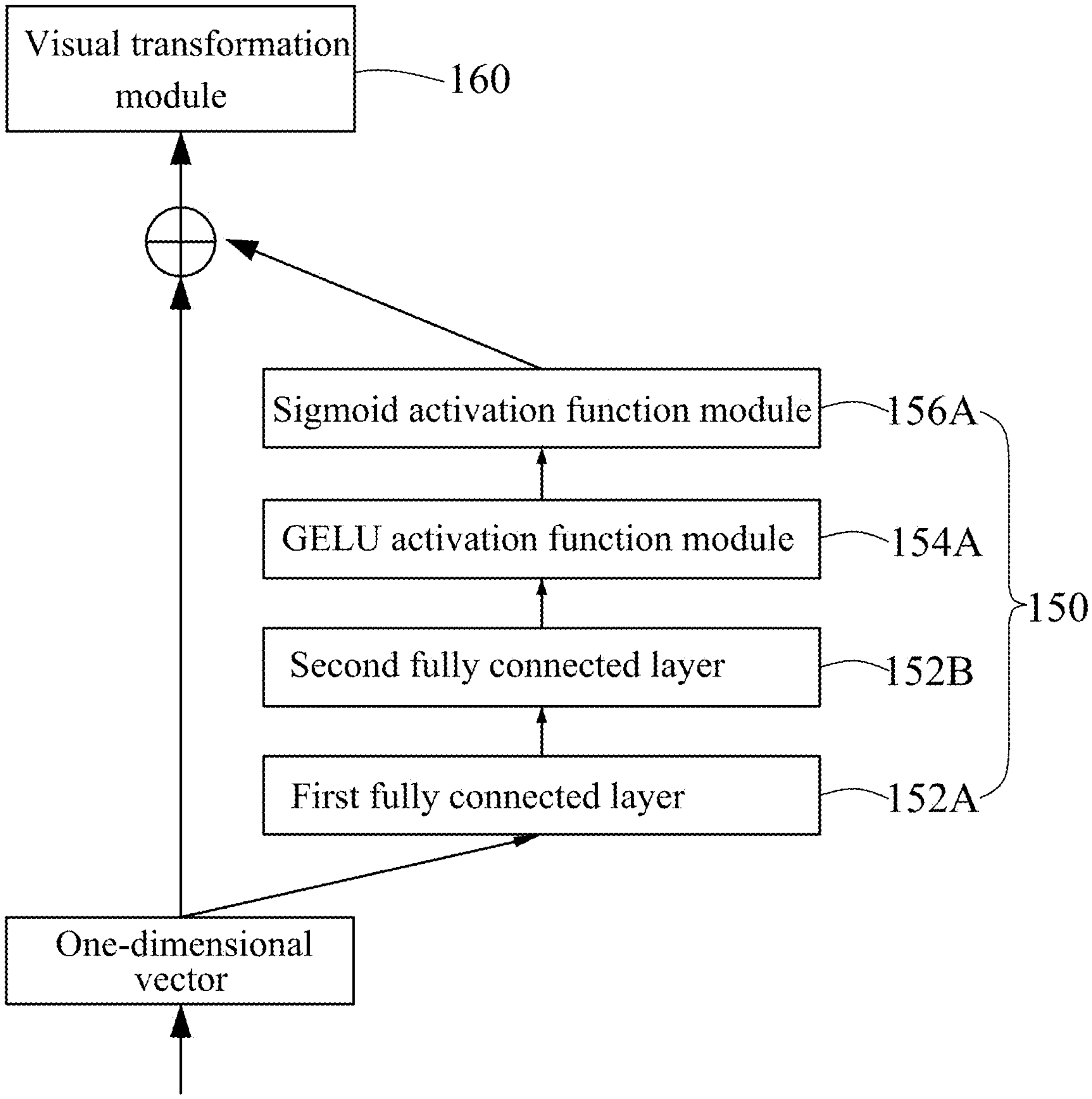
FIG. 5B illustrates one implementation of the positional embedding module in this disclosure.

Additionally, one implementation of the structure of the positional embedding module 150 is shown in FIG. 5B. Firstly, the positional embedding module 150 includes a first fully connected layer 152A, which is used for linear transformation of the one-dimensional vector of the block 11. A fully connected layer is a basic component in neural networks, its function is to connect each input node (or neuron) to each output node. Here, the role of the first fully connected layer 152A is to perform a linear transformation of the one-dimensional vector of the block, to extract higher-level features. Furthermore, the positional embedding module 150 also includes a second fully connected layer 152B, which is connected to the first fully connected layer 152A, and is used to further linearly transform the output of the first fully connected layer 152A. This is to further extract and transform features, in order to better capture complex patterns in the one-dimensional vector of the block 11. The positional embedding module 150 also includes a GELU activation function module 154A, which is connected to the second fully connected layer 152B, and is used to introduce non-linearity to the output of the second fully connected layer 152B. The GELU activation function module 154A is a commonly used activation function, it can introduce non-linearity, allowing the positional embedding module 150 to learn and represent more complex functions. In addition, the positional embedding module 150 also includes a Sigmoid activation function module 156A, which is connected to the GELU activation function module 154A, and is used to transform the output value of the GELU activation function module 154A to the range [0, 1]. The Sigmoid activation function module 156A is a function that compresses real numbers to between 0 and 1, this allows the output of the model to be interpreted as a probability.

In FIG. 5B, the first fully connected layer 152A and the second fully connected layer 152B correspond to the feature extraction module 152 in FIG. 5A, the GELU activation function module 154A corresponds to the activation function module 154 in FIG. 5A, and the normalization module 156 corresponds to the normalization module 156 in FIG. 5A. Of course, those of ordinary skill in the art can adopt different implementations as needed. For example, the feature extraction module 152 can include more or better fully connected layers, the activation function module 154 can be a Max out activation function, RELU activation function, or SELU activation function, and the normalization module 156 can be a general normalization formula.

In summary, the positional embedding module 150 can extract useful features from the one-dimensional vector of the block 11, and transform these features into a form that allows the model to learn and predict better.

Figure 6:
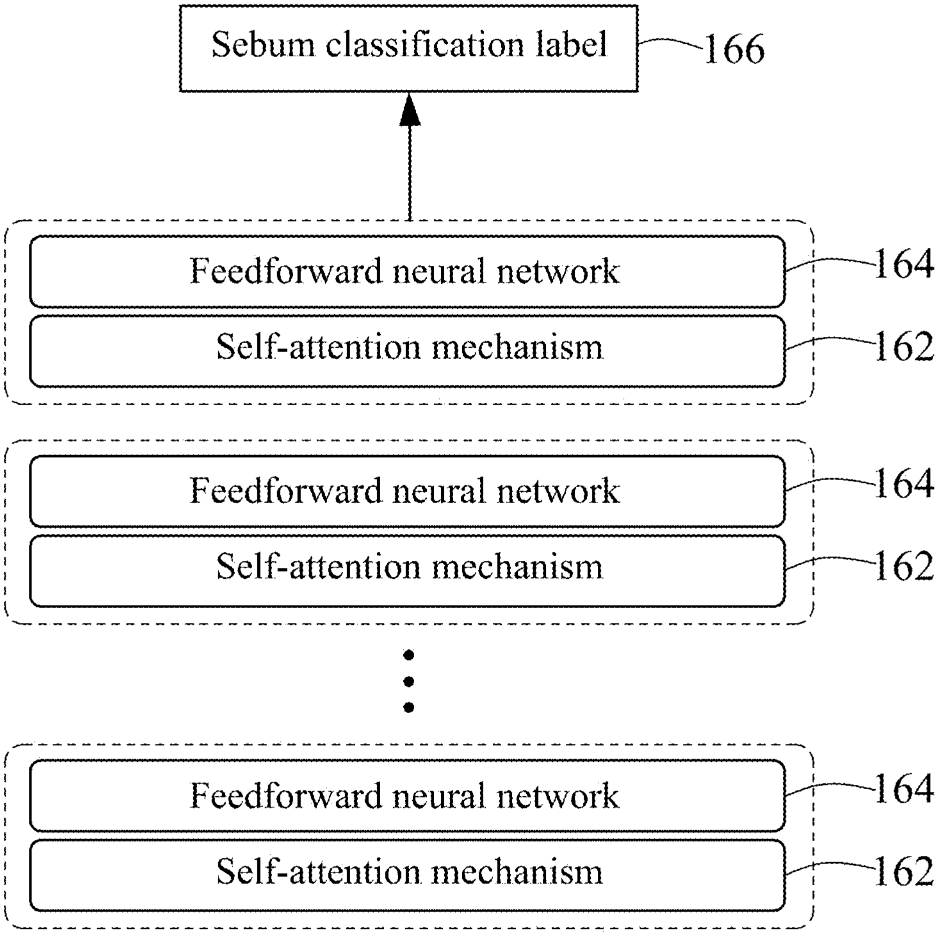
FIG. 6 illustrates a schematic diagram of the visual transformation model in this disclosure.

Referring to FIG. 6, the visual transformation model 160 is the core component of the automatic scalp sebum classification system 100, responsible for processing the input vectors and outputting the sebum classification label. The visual transformation model 160 is an artificial intelligence model designed for image analysis tasks. It is based on the Transformer architecture, which was originally developed for natural language processing tasks, but has been adapted for computer vision.

The visual transformation model 160 contains a plurality of layers of self-attention mechanisms 162 and feedforward neural networks 164. The self-attention mechanisms 162 allow the visual transformation model 160 to focus on different parts of the input data based on their relevance to the task at hand. In this implementation, the self-attention mechanisms 162 allow the visual transformation model 160 to focus on different blocks 11 of the scalp image 10, giving more attention to blocks that contain more information for the sebum classification task.

Each layer of the self-attention mechanism 162 in the visual transformation model 160 operates by calculating the weighted sum of the input vectors, where the weights are determined by the relevance of each vector to the other vectors. This relevance is quantified using a measure called attention scores, which is calculated based on the similarity between vectors. The attention scores are then used to weight the input vectors, allowing the visual transformation model 160 to focus more on vectors with higher scores.

The feedforward neural networks 164 in the visual transformation model 160 are used to transform the weighted sum of the input vectors into a higher-level representation. These feedforward neural networks 164 consist of a plurality of layers of neurons, each layer performing a linear transformation on its input, followed by a non-linear activation function. The output of the feedforward neural networks 164 is a set of feature vectors, capturing high-level patterns in the input data.

The visual transformation model 160 processes the input vectors in a sequential manner, passing them through a plurality of layers of self-attention mechanisms 162 and feedforward neural networks 164. At each layer, the visual transformation model 160 updates the feature vectors based on the information extracted from the previous layer. This iterative process allows the visual transformation model 160 to gradually refine its understanding of the input data, leading to more accurate sebum classification results.

Finally, the visual transformation model 160 outputs a sebum classification label 166 based on the final set of feature vectors. This sebum classification label 166 indicates the sebum properties of the scalp part represented by the input image, and can be one of the following three categories: dry, neutral, or oily. The sebum classification label 166 serves as the final output of the automatic scalp sebum classification system 100, providing a concise indication of the analyzed scalp sebum properties.

In summary, the two main technical improvements of the automatic scalp sebum classification system 100 contribute greatly to its performance and privacy protection: the random rotation and position swapping of blocks 11, and the use of learnable position embeddings.

The random rotation and position swapping of blocks 11 is performed by the data augmentation module 130. The data augmentation module 130 introduces a degree of randomness into the data, which has two main purposes. First, it enhances the robustness of the visual transformation model 160 by exposing it to a wider range of data scenarios. This is particularly beneficial in addressing the problem of class imbalance, where some sebum property categories may be underrepresented in the training data. By randomly rotating and swapping the positions of the blocks 11, the automatic scalp sebum classification system 100 effectively increases the diversity of training data for each category, helping to mitigate the impact of class imbalance and improve the overall performance of the model.

Second, the random rotation and position swapping of the blocks 11 serve as a privacy protection measure. By scrambling the original arrangement of the blocks 11, the automatic scalp sebum classification system 100 makes it difficult to reconstruct the original scalp image, thereby protecting individual privacy. This feature is particularly valuable in applications where personal privacy is paramount, such as in medical diagnosis or personal care applications.

Another notable technical improvement in the automatic scalp sebum classification system 100 is the use of learnable embedding vectors. This feature is implemented by the positional embedding module 150, which adds a layer of spatial information to the one-dimensional vector representing each block 11, allowing the automatic scalp sebum classification system 100 to retain some spatial context. This is particularly beneficial for the visual transformation model 160, as it allows the visual transformation model 160 to adapt to specific spatial relationships in the data, thereby achieving more accurate classification.

In conclusion, the random rotation and position swapping of blocks 11, and the use of learnable embedding vectors, are the two main technical improvements in the automatic scalp sebum classification system 100 of this disclosure. These improvements enhance its performance and protect privacy. These features ensure that the automatic scalp sebum classification system 100 can handle subtle feature differences and class imbalance in the data, while ensuring the privacy of the scalp images being analyzed.

What is claimed is:

1. A method for automatic classification of scalp sebum, comprising the following steps:

capturing a high-resolution image of a part of a scalp;

dividing the image into a plurality of non-overlapping blocks;

randomly rotating and swapping positions of the blocks;

converting each block into a one-dimensional vector;

adding positional information to the one-dimensional vector through learnable embedding vectors;

inputting the learnable embedding vectors into a visual transformation model; and outputting a sebum classification label based on the analysis of the visual transformation model.

2. The method for automatic classification of scalp sebum of claim 1, wherein the step of adding positional information to the one-dimensional vector through learnable embedding vectors comprises:

transforming the one-dimensional vector through at least one feature extraction step;

applying at least one activation function to introduce non-linearity in the output of the feature extraction step; and normalizing the output value through a normalization step.

3. The method for automatic classification of scalp sebum of claim 2, wherein the feature extraction step includes a linear transformation performed by a first fully connected layer and a second fully connected layer, applying the activation function step includes applying a GELU activation function for introducing non-linearity, and the normalization step includes a Sigmoid activation function module for normalizing the output values to a range between 0 and 1.

4. The method for automatic classification of scalp sebum of claim 1, wherein the visual transformation model includes a plurality of layers of self-attention mechanisms and feedforward neural networks.

5. The method for automatic classification of scalp sebum of claim 1, wherein the sebum classification label includes: dry, neutral, or oily.

6. The method for automatic classification of scalp sebum of claim 1, wherein the random rotation and position swapping of blocks are for enhancing privacy protection.

7. The method for automatic classification of scalp sebum of claim 1, wherein the visual transformation model outputs the sebum classification label in real-time.

8. The method for automatic classification of scalp sebum of claim 1, wherein the blocks are square-shaped.

9. The method for automatic classification of scalp sebum of claim 1, wherein the one-dimensional vector and learnable embedding vectors are concatenated before being input into the visual transformation model.

* * * * *